United States Patent
Kassin et al.

(10) Patent No.: US 10,428,461 B1
(45) Date of Patent: Oct. 1, 2019

(54) TOILET TISSUE SPRAY DISPENSER AND METHOD

(71) Applicants: Joseph Kassin, Brooklyn, NY (US); Michael Kassin, Brooklyn, NY (US)

(72) Inventors: Joseph Kassin, Brooklyn, NY (US); Michael Kassin, Brooklyn, NY (US)

(73) Assignee: Aquinelle, LLC, New York, NY (US)

( * ) Notice: Subject to any disclaimer, the term of this patent is extended or adjusted under 35 U.S.C. 154(b) by 0 days.

(21) Appl. No.: 15/060,427

(22) Filed: Mar. 3, 2016

Related U.S. Application Data

(60) Provisional application No. 62/127,482, filed on Mar. 3, 2015.

(51) Int. Cl.
| | |
|---|---|
| *D21H 23/50* | (2006.01) |
| *B05D 1/02* | (2006.01) |
| *E03D 9/00* | (2006.01) |
| *A61L 2/22* | (2006.01) |

(52) U.S. Cl.
CPC .......... *D21H 23/50* (2013.01); *A61L 2/22* (2013.01); *B05D 1/02* (2013.01); *E03D 9/007* (2013.01)

(58) Field of Classification Search
CPC .. D21H 23/50; A61L 2/22; B05D 1/02; E03D 9/007
See application file for complete search history.

(56) References Cited

U.S. PATENT DOCUMENTS

| | | | | |
|---|---|---|---|---|
| 3,776,773 | A * | 12/1973 | Taft | A47K 10/32 118/325 |
| 4,598,664 | A * | 7/1986 | Hamlin | A47K 10/32 118/32 |
| 5,887,759 | A * | 3/1999 | Ayigbe | A47K 10/32 118/325 |
| 5,980,919 | A * | 11/1999 | Greenfield | D21H 21/22 239/3 |
| 6,162,329 | A * | 12/2000 | Vinson | D21H 21/22 162/112 |
| 6,314,971 | B1 * | 11/2001 | Schneider | A47K 10/32 134/122 R |
| 6,497,345 | B1 * | 12/2002 | Wilker | A47K 10/32 222/130 |
| 6,675,405 | B1 * | 1/2004 | Harm | E03D 9/085 239/282 |

(Continued)

FOREIGN PATENT DOCUMENTS

WO   WO-2011083401 A2 *  7/2011 .......... A61K 8/0208

*Primary Examiner* — Regina M Yoo
(74) *Attorney, Agent, or Firm* — Goldberg Cohen LLP

(57) ABSTRACT

A toilet tissue mist with a liquid discharge device for spray application to toilet paper. The liquid dispensed onto the paper in small quantities is for personal cleansing of the human body and results in a cleansing and freshening up of the selected areas. The mist turns the toilet paper into the equivalent of a wet wipe or cloth which would be soothing to sensitive areas. Likewise, the mist is scented and helps freshen up any unwanted odors. The device is portable and compact and may be used on the go as well as being used at home. Likewise, the resulting moistened wipe can be discarded by flushing it down the toilet, just like regular toilet paper. In a preferred embodiment, the device is configured to provide a diameter of mist to the toilet tissue with a dry outline circumscribing it.

8 Claims, 2 Drawing Sheets

(56) References Cited

U.S. PATENT DOCUMENTS

| | | | | |
|---|---|---|---|---|
| 7,578,388 | B2 * | 8/2009 | O'Connell | B05C 17/002 |
| | | | | 206/223 |
| 8,827,116 | B1 * | 9/2014 | Hamilton | A47K 5/1202 |
| | | | | 222/180 |
| 2003/0132314 | A1 * | 7/2003 | Neuendorf | A47K 10/32 |
| | | | | 239/333 |
| 2008/0138144 | A1 * | 6/2008 | Kennedy | A45D 34/04 |
| | | | | 401/188 R |
| 2009/0170744 | A1 * | 7/2009 | Meine | C11D 3/0063 |
| | | | | 510/302 |
| 2010/0163580 | A1 * | 7/2010 | Ophardt | A47K 5/1207 |
| | | | | 222/181.3 |
| 2012/0248136 | A1 * | 10/2012 | Meyers | A61L 2/22 |
| | | | | 221/96 |
| 2014/0034680 | A1 * | 2/2014 | Kennedy | B05B 11/3009 |
| | | | | 222/205 |
| 2014/0318448 | A1 * | 10/2014 | Hug | A47K 10/32 |
| | | | | 118/620 |
| 2016/0213004 | A1 * | 7/2016 | Weisman | A01N 63/00 |

* cited by examiner

TOILET TISSUE SPRAY DISPENSER AND METHOD

CROSS REFERENCE TO RELATED APPLICATION

This application claims the benefit of U.S. Provisional Patent Application Ser. No. 62/127,482, filed Mar. 3, 2015, which is fully incorporated herein by reference.

BACKGROUND OF THE INVENTION

It is a pervasive and common problem that regular toilet paper is all that is provided in most bathrooms, especially public bathrooms. However, regular toilet paper is dry and can irritate sensitive areas. As a result, individuals often prefer to use wet wipes or moistened tissues to soothe and moisturize selected areas, but they are not always available.

Likewise, individuals often prefer to use pre-moistened wipes as they have the added benefit of allowing the user to cleanse and freshen up selected areas. Regular toilet paper does not have the same hygienic and cleansing abilities.

Yet a further disadvantage of using regular toilet paper is that it is unscented. However, moistened wipes can have a scent to mask unwanted odors.

Wet wipes currently exist on the market and are often used for small children wearing diapers. However, wet wipes are usually unavailable in adult restrooms. Moreover, it is inconvenient to have to carry around a package of wet wipes all the time, as they are heavy and can take up a lot of space. Although mothers who have babies typically carry around a diaper bag with bulky supplies, adults usually do not want to carry around cumbersome items. Also, if wet wipes are not used shortly after the package is opened they can dry up and go to waste, so they must be in a sealed enclosure to prevent the wipes from drying out.

Also, some wet wipes are not designed to be flushed down the toilet, so they must be disposed of in a trash can in order to prevent blockage in internal plumbing and clogged sewer systems. Even the wipes that are marketed as flushable can cause plumbing issues. For example, a recent Consumer Reports test revealed that a sheet of toilet paper can fall apart about eight seconds in swirling water, while a "flushable" wipe did not fray after half an hour.

Accordingly, there is a considerable need for a product that provides a solution to the problems in the art.

SUMMARY OF THE INVENTION

The present invention provides a solution for the problems and shortcomings of the current existing toilet papers and wet wipes, and is particularly beneficial for use on the go and during travel. In the present invention, a device is provided with a liquid which can be sprayed out onto toilet paper whenever the user wants to turn regular toilet paper into a moistened toilet tissue or type of wet wipe. The present invention thus provided a compact and portable means of creating a moistened toilet tissue or type of "wet wipe" from regular toilet paper.

In a further aspect of the invention, a product is provided for moistening toilet tissue, wherein the characteristics of the spray dispenser, the liquid in the dispenser, and the fragrance in the liquid, are chosen such that use of the dispenser to spray liquid onto the toilet paper to moisten the tissue concurrently dissipates fragrance into the air. In this manner, the product serves the multiple purposes of moistening the toilet tissue for cleansing and moisturizing the consumer's skin, as well as freshening the bathroom air.

One embodiment is generally directed to a toilet tissue mist spray dispenser comprising a spray bottle defining an interior. A quantity of cleansing liquid is retained within the spray bottle interior. A spray cap that is selectively removable from a top of the spray bottle has a finger pump for extracting the cleansing liquid. The finger pump further defines an orifice for dispensing the cleansing fluid through the orifice as a cone of mist. The cone of mist has an approximate diameter of three inches at a distance of approximately four inches from the orifice.

In another aspect, the cleansing liquid is a hygienic liquid.

In still another aspect, the cleansing liquid is scented.

In yet another aspect, the dispenser when oriented at approximately four inches from and at approximately 45 degrees to a square of toilet tissue deposits approximately a three inch diameter circle of cleansing liquid on the toilet tissue.

In a still further aspect, the dispenser when oriented at approximately four inches from and at approximately 45 degrees to a four inch square of toilet tissue, deposits a quantity of cleansing liquid to a center portion of the toilet tissue and leaves approximately a one inch dry outline about the toilet tissue square.

In another aspect, the cleansing liquid is formulated with:
Water 30%-100%;
Cocamidopropyl 3%-30%;
PEG 80 Sorbitan Laurate 3%-30%;
Sodium Trideceth Sulfate 3%-30%;
PEG 150 Distearate 3%-30%;
Glycerin 3%-30%;
Propylene Glycol 3%-30%;
1,3 Propanediol 1%-3%;
Ethylhexyl Glycerin 1%-3%;
Potassium Sorbate 1%-3%;
*Hamamelis Virginiana* Extract 0.1%-0.3%;
Glycerin 0.1%-0.3%;
Aloe Barbadensis Leaf Juice 0.1%-0.3%;
Tocopheryl Acetate 0.1%-0.3%;
Sodium Benzoate 0.1%-0.3%;
Potassium Sorbate 0.1%-0.3%;
Phenoxyethanol 0.1%-0.3%;
Citric Acid 0.1%-0.3%;
Aloe Barbadensis Leaf Juice >0%-0.1%;
Tocopheryl Acetate >0%-0.1%; and
Citric Acid >0%-0.1%.

In another aspect, the cleansing liquid further includes:
Fragrance 0.1%-0.3%.

In another embodiment, a method of wetting a toilet tissue square with a quantity of cleansing liquid to create a moistened wipe includes the steps of acquiring a dispenser of the type having a spray bottle with a quantity of cleansing liquid retained therein and further having a spray cap affixed to a top of the spray bottle. The spray cap has a finger pump for extracting the cleansing liquid and further defines an orifice for dispensing the cleansing fluid through the orifice as a cone of mist having an approximate diameter of three inches at a distance of approximately four inches from the orifice. At least one square of toilet tissue is acquired that is approximately four inches square. The dispenser is held approximately four inches from the toilet tissue square, and the orifice of the finger pump is oriented at an angle with respect to a plane of the toilet tissue. The finger pump is depressed at least once to dispense a cone of mist of the cleansing liquid toward the toilet tissue square. A portion of the cone of mist is allowed to deposit on the toilet tissue square to moisten the toilet tissue square. The toilet tissue square is then applied to an area of the user's body desired to be cleansed.

In yet another aspect, a plurality of toilet tissue squares are acquired and arranged in a stacked configuration.

In another aspect, in the orienting step the angle of orientation of the orifice is within the range of 30 degrees to 60 degrees.

In still another aspect, in the orienting step, the orifice is angled at 45 degrees with respect to the plane of the toilet tissue square.

In yet another aspect, in the depressing the finger pump step, the finger pump is depressed three times to accumulate three spray mists on the toilet tissue square.

In another aspect, in the depressing the finger pump step, the finger pump is depressed at least once to moisten a center section of the toilet tissue square while leaving an outer outline portion dry.

In still another aspect, the cleansing liquid is formulated with:
Water 30%-100%;
Cocamidopropyl 3%-30%;
PEG 80 Sorbitan Laurate 3%-30%;
Sodium Trideceth Sulfate 3%-30%;
PEG 150 Distearate 3%-30%;
Glycerin 3%-30%;
Propylene Glycol 3%-30%;
1,3 Propanediol 1%-3%;
Ethylhexyl Glycerin 1%-3%;
Potassium Sorbate 1%-3%;
*Hamamelis Virginiana* Extract 0.1%-0.3%;
Glycerin 0.1%-0.3%;
Aloe Barbadensis Leaf Juice 0.1%-0.3%;
Tocopheryl Acetate 0.1%-0.3%;
Sodium Benzoate 0.1%-0.3%;
Potassium Sorbate 0.1%-0.3%;
Phenoxyethanol 0.1%-0.3%;
Citric Acid 0.1%-0.3%;
Aloe Barbadensis Leaf Juice >0%-0.1%;
Tocopheryl Acetate >0%-0.1%; and
Citric Acid >0%-0.1%.

In yet another aspect, the cleansing liquid further includes:
Fragrance 0.1%-0.3%.

In yet another aspect, a product is provided for use to spray a mist onto toilet tissue, such that the tissue is lightly moistened, but without applying an undue amount of liquid to the toilet tissue. In this aspect, the volume of liquid applied from a single spray is not so large as to soak the tissue or user's hands, or to cause the toilet tissue to disintegrate from an excessive amount of liquid.

These and other features, aspects, and advantages of the invention will be further understood and appreciated by those skilled in the art by reference to the following written specification, claims and appended drawings.

BRIEF DESCRIPTION OF THE DRAWINGS

The preferred embodiments of the invention will hereinafter be described in conjunction with the appended drawings provided to illustrate and not to limit the invention where like designations denote like elements, and in which.

DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The present invention relates to the field of cleansing products. It can be utilized anywhere, but is particularly useful for use in a home or office bathroom, and on the go, and for travel.

Figure 1:
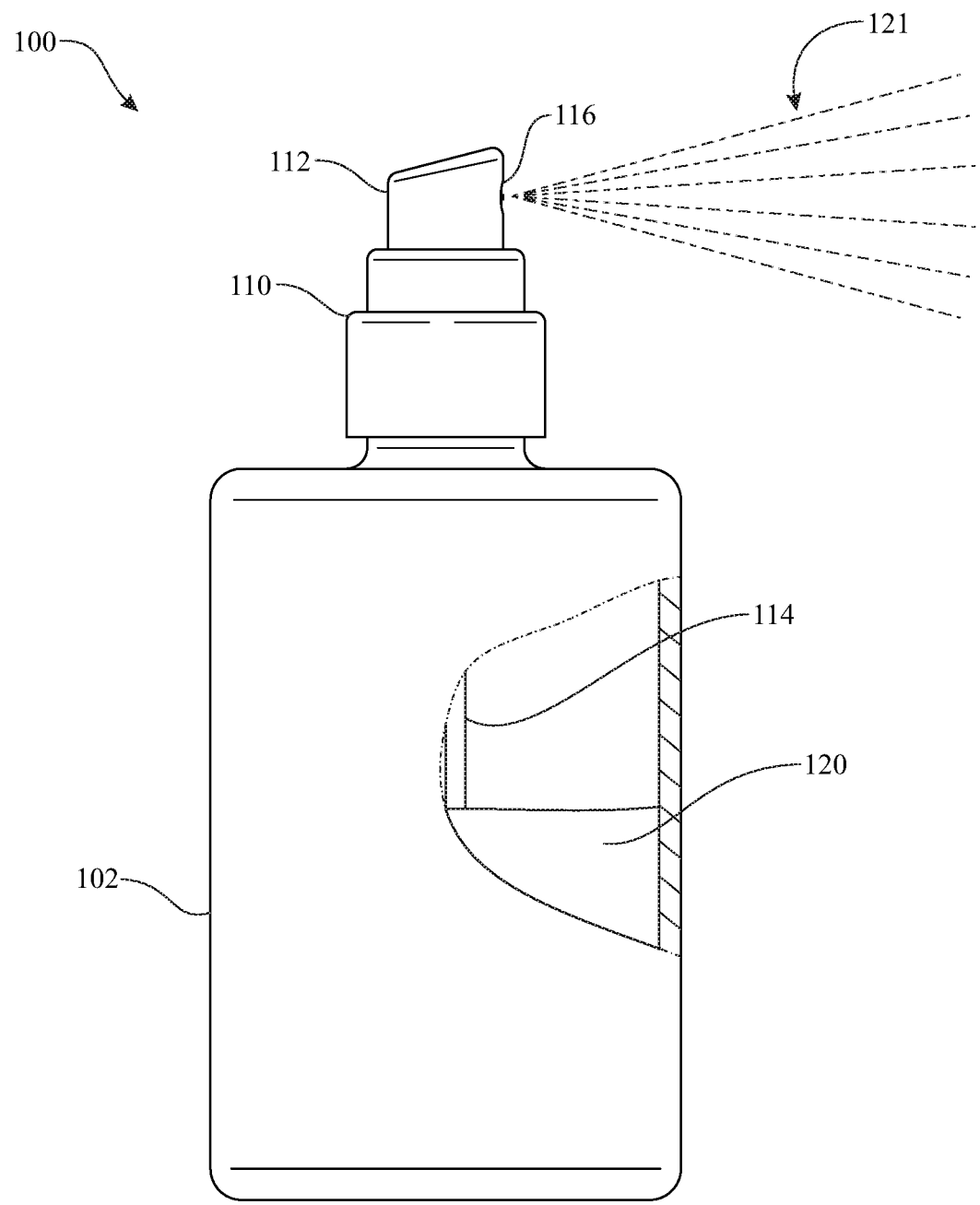
FIG. 1 presents an elevation view of a liquid dispenser with a quantity of liquid therein for dispensing onto toilet tissue.
Figure 2:
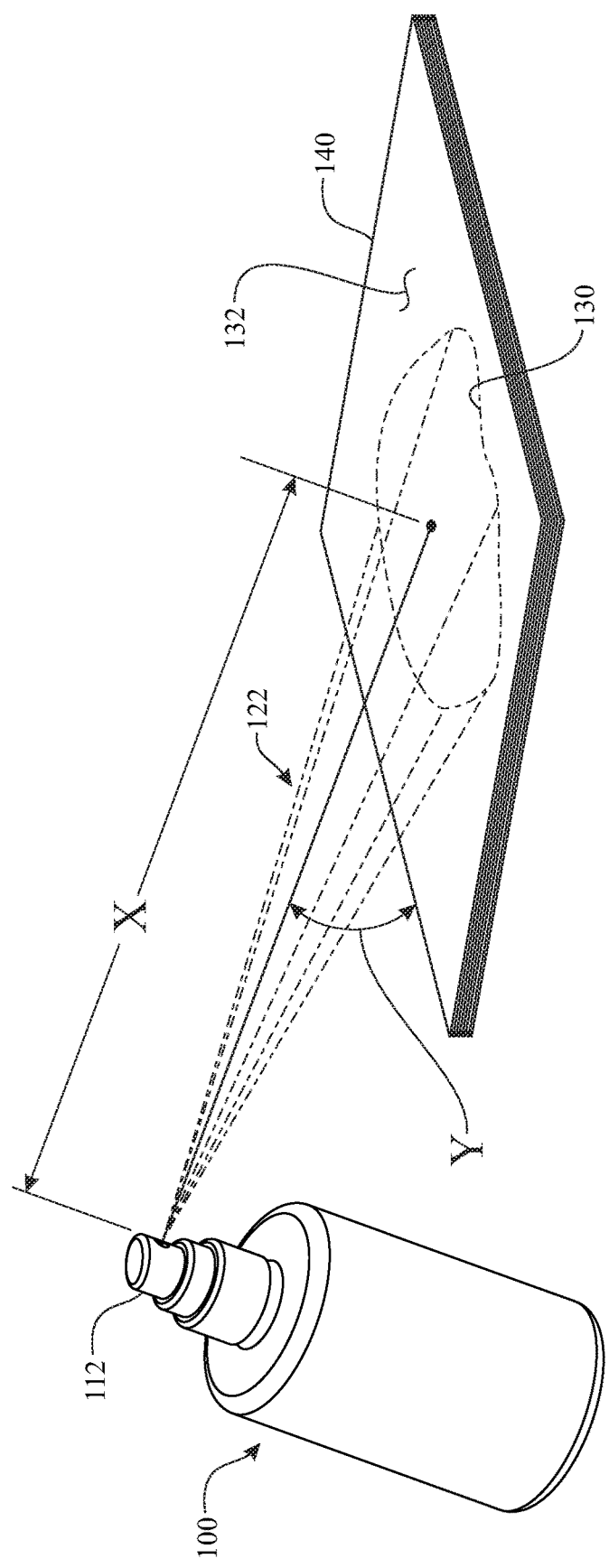
FIG. 2 presents an isometric view of the liquid being dispensed from the dispenser onto a square of toilet tissue.

Turning now to FIGS. 1-2, and in accordance with the invention, a toilet tissue mist spray dispenser 100 is provided which enables the user to turn regular toilet paper into a moistened toilet tissue or type of wet wipe. This device is a spray bottle 102 containing a cleansing liquid 120, wherein the cleansing liquid 120 may be selectively dispensed on the toilet paper by means of a spray cap 110 which permits the cleansing liquid 120 to be squirted in controlled quantities directly onto the toilet paper 140. The liquid is applied to the toilet paper 104 in mist form 122 as not to tear the toilet paper due to excessive wetness. Depending on how much liquid 120 is desired, the individual many increase the number of sprays applied to the toilet paper 140.

The liquid can be a fluid spray or mist 122. The cleansing liquid 120 serves to moisten the toilet paper. The spraying of the aforementioned liquid 120 onto a sheet of toilet paper 140 would effectively turn the toilet paper 140 into a moistened wipe which is useful for moisturizing and soothing sensitive areas of human skin. In a preferred embodiment, the invention is used to create a moistened wipe, rather than a wet wipe, as consumers may prefer it when the wipe is not oversaturated with liquid. The lubrication of the skin due to the moisture on the toilet paper sheet 140 can help prevent rashes and irritation of the skin and sensitive areas.

Likewise, the liquid 120 is hygienic and can be used for personal cleansing of certain areas of the body whenever required. The liquid 120 in the bottle contains a solution formulated to clean the skin and provide for personal hygiene. The moisture contained on the sheet 140 can have a refreshing effect and can be used throughout the day to freshen up. Additionally, the spray or mist 122 can be provided with a pleasant scent which is used to mask any bad bodily odors and can serve to further freshen up the body parts that it is applied to.

As best shown in FIG. 1, the structure of the device 100 is a bottle 102 defining an interior containing a quantity of cleansing liquid 120 and a spray cap 110 to facilitate easy dispensing. The spray cap 110 has a supply tube 114 for drawing the cleansing liquid 120 into the spray cap 110 for discharge from nozzle orifice 116. With each press of the finger pump 112, the device 100 sprays out a mist 121 from the orifice 116 in a specific predetermined force and concentration which is designed to lightly or moderately moisten the toilet paper 140 but not pierce through the sheet of toilet paper 140. Excessive moisture tends to tear toilet paper, so the device controls the amount of each spray. Furthermore, the mist 121 is gentle and spreads the cleansing liquid 120 enough that it comes out as a gentle spray 121 rather than a stream. As shown in FIG. 2, the liquid 120 is applied in a specific concentration which provides the transfer of an effective amount of mist 122 onto the sheet of toilet paper 140 which creates a moisturizing texture when applied to the sheet 140. The sheet 140 then transfers the moisture to the body when rubbed against the skin or the particular body part of the user's choice.

In a preferred embodiment of the invention, the spray dispenser 100 is configured to provide a cone of mist 122 wherein having a configuration with a diameter of mist 130 that will moisten a particular desired proportion of the area of a square of toilet paper 140, and leave a particular desired proportion of the toilet paper as a dry outline 132. In one such embodiment, a majority 130 of the toilet tissue square 140 (measured based on either the area or based on the diameter of the square) is moistened, with a dry area 132 left circumscribing the dry area, when the mist 122 from the bottle is sprayed onto the toilet paper at a particular distance "X". In further embodiments, two thirds of either the diameter or of the area, or three quarters of either the diameter or of the area, are moistened at a particular distance "X". In the preferred embodiment the distance "X" is approximately 4 inches. Further, the mist 122 is directed at the toilet tissue 140 at an angle "Y" between 30 degrees and 60 degrees and, in the preferred embodiment, the angle "Y" is 45 degrees. In yet further embodiments, less than a majority of either the diameter or of the area, or more than three quarters of either the diameter or of the area thereof are moistened at a particular distance.

For example, in the United States, the typical toilet tissue sheet is approximately a 4 inch×4 inch square. Thus, in a preferred embodiment of the invention, the dispenser is configured to produce an output of 0.61 grams of cleansing liquid 120 per depression of the finger pump 112 which provides a circle of approximately 3 inches in diameter when held at a 4 inch distance from the spray bottle 100 to toilet tissue 140 when the mist 122 is oriented at approximately 45 degrees to the plane of the toilet tissue 140. Preferably, a plurality of toilet tissue squares 140 are arranged in a stacked configuration. Each depression of the finger pump 112 will output approximately 0.61 grams of the cleansing liquid from the nozzle orifice 116 as the mist 122. However, not all of the mist 122 is deposited on the toilet tissue 140 at the 45 degree orientation. Of the 0.61 grams in the mist 122, approximately 0.51 grams are deposited on the toilet tissue 140. Typically, three pumps of the finger pump 112 are required to obtain a preferred amount of cleansing liquid 120 on the toilet tissue 140. The three pumps of finger pump 112 will give the user a circle of 3 inch diameter of moistened tissue 130 to clean with, and an approximately 1 inch width dry outline 132 around the edge of the 4 inch toilet tissue. (The exact width of the dry outline that surrounds the moist area will vary slightly due to the fact that a moist circle is being imposed onto a square). Preferably, this amount of liquid is dispensed to this diameter with three pushes of the delivery system 110, in order to effectively moisten the toilet tissue with minimal effort, although the system can be designed for any desired number of pushes, whether one to three or greater.

Likewise, in further embodiments, a spray dispenser 100 is provided for any other country which provides a mist 122 of desired circular size 130 onto the toilet paper tissue 140 of that region, while leaving a dry outline 132 around the circular moist area 130.

The present invention can come in a spray bottle of various sizes, each with its own set of specifications. Two such examples are as follows:
Spray details for a 3 oz bottle (e.g. for pocket or travel use):
Pump Specifications
Dip tube: 115 mm (+/−1.5 mm) (from base of gasket)
Fixture: 24-410
Bottle Dimensions
H Dimension: 0.657" (SPI Specification 0.631"-0.661")
Land: 0.045" (Suggested 0.050" minimum)
Spray details for an 8 oz bottle (e.g. to leave in home or office bathrooms):
Pump Specifications
Dip tube: 115 mm (+/−1.5 mm) (from base of gasket)
Fixture: 24-410
Bottle Dimensions
H Dimension: 0.657" (SPI Specification 0.631"-0.661")
Land: 0.045" (Suggested 0.050" minimum)

Any desired size bottle of liquid can be used with that pump 110 (or another suitable pump), consistent with the present invention.

Within the dispenser, a suitable liquid 120 is provided for hygienically cleansing the body of fecal matter. As an example, in one embodiment any liquid can be utilized such as those liquids that are currently applied to wet wipes, whether baby wet wipes or those marketed for adults. Preferably, the liquid 120 is scented to freshen the body with a pleasant smell, although an unscented liquid can alternatively be used. A preferred formulation for the cleansing liquid 120 is listed in Table 1 below.

Accordingly, the present invention allows a user to create a moistened toilet tissue or wet wipe for use on babies or adults. It allows one to moisten the toilet paper 140, and then to discard the toilet paper 140 in the regular manner, by flushing it down the toilet. This makes the toilet paper 140 easy to use and discard. It also makes the toilet paper 140 more efficient at lifting and removing fecal matter and other waste from the user's body, and in cleansing, deodorizing, freshening, and moisturizing the body in a more hygienic manner than dry toilet paper alone.

Moreover, in accordance with the invention, toilet tissue of regular texture is used, avoiding materials which would prevent the product from being flushed down the toilet. This is unlike wet wipes which must be discarded in the trash when they are not designed to be flushed down the toilet (thus leaving unhygienic waste in the trash), and which can cause plumbing problems even if they are designed for flushing.

TABLE 1

Cleansing Liquid Formulation

| Ingredient | Concentration | Function |
| --- | --- | --- |
| Water | 30%-100% | Carrier |
| Cocamidopropyl | 3%-30% | Surfactant |
| PEG 80 Sorbitan Laurate | 3%-30% | Emulsifier |
| Sodium Trideceth | 3%-30% | Surfactant |

TABLE 1-continued

Cleansing Liquid Formulation

| Ingredient | Concentration | Function |
|---|---|---|
| Sulfate | | |
| PEG 150 Distearate | 3%-30% | Emulsifier |
| Glycerin | 3%-30% | Humectant |
| Propylene Glycol | 3%-30% | Moisturizer |
| 1,3 Propanediol | 1%-3% | Emollient |
| Ethylhexyl Glycerin | 1%-3% | Improves Skin Feel |
| Potassium Sorbate | 1%-3% | Anti-microbial |
| Hamamelis Virginiana Extract | 0.1%-0.3% | Skin Conditioner |
| Glycerin | 0.1%-0.3% | Humectant |
| Aloe Barbadensis Leaf Juice | 0.1%-0.3% | Skin Conditioner |
| Tocopheryl Acetate | 0.1%-0.3% | Skin Conditioner |
| Sodium Benzoate | 0.1%-0.3% | Anti-microbial |
| Potassium Sorbate | 0.1%-0.3% | Anti-microbial |
| Phenoxyethanol | 0.1%-0.3% | Anti-microbial |
| Citric Acid | 0.1%-0.3% | Preservative & pH |
| Aloe Barbadensis Leaf Juice | >0%-0.1% | Skin Conditioner |
| Tocopheryl Acetate | >0%-0.1% | Skin Conditioner |
| Citric Acid | >0%-0.1% | pH Adjuster |
| Fragrance | 0.1%-0.3% | Perfume |
| Color Dye | >0%-0.1% each | Dye |

In addition, the present invention provides a compact, portable device as a liquid dispenser 100 which can be used anywhere and anytime. Instead of having to rely on finding special wet wipes in a bathroom (especially public bathrooms which would not have them), the invention gives the user a portable solution which is very useful for travel. The user can keep this small bottle of liquid in his or her bag or pocket and take it out at any time needed to turn regular toilet paper into a moistened wipe which can serve all the purposes described above.

Yet furthermore, the invention provides a device configured to effectively moisten a large proportion of the area of the toilet tissue square, while preferably also leaving a rim of dry tissue (unlike traditional wipes). This provides both ease of handling, and a product which may be preferred by many users.

As such, in accordance with the features described above, the invention solves many of the shortcomings of the current existing toilet paper and other wipe options available on the market.

Although the above description is provided to describe and illustrate examples of certain embodiments of the present invention, modifications of the invention will occur to those skilled in the art and to those who make or use the invention. Therefore, it is understood that the embodiments described herein are merely for illustrative purposes only and are not intended to limit the scope of the invention as set forth in issued claims.

What is claimed is:

1. A method of moistening a toilet tissue square with a quantity of cleansing liquid to create a moistened wipe, said method comprising the steps of:
    acquiring a portable dispenser of the type having a spray bottle with a quantity of cleansing liquid retained therein and further having a spray cap affixed to a top of the spray bottle, the spray cap having a finger pump for extracting the cleansing liquid and further defining an orifice for dispensing the cleansing liquid through the orifice as a cone of mist having an approximate diameter of three inches at a distance of approximately four inches from the orifice;
    acquiring at least one square of toilet tissue approximately four inches square;
    holding the dispenser in a user's hand approximately four inches from the at least one toilet tissue square;
    orienting the orifice of the finger pump at an angle with respect to a plane of the toilet tissue;
    depressing the finger pump at least once to dispense a cone of mist of the cleansing liquid toward the at least one toilet tissue square;
    allowing a portion of the cone of mist to deposit on the at least one toilet tissue square to moisten the at least one toilet tissue square; and
    applying the at least one toilet tissue square to an area of the user's body desired to be cleansed;
    wherein the cleansing liquid is formulated with:
    Water 30%-100%;
    Cocamidopropyl 3%-30%;
    PEG 80 Sorbitan Laurate 3%-30%;
    Sodium Trideceth Sulfate 3%-30%;
    PEG 150 Distearate 3%-30%;
    Glycerin 3%-30%;
    Propylene Glycol 3%-30%;
    1,3 Propanediol 1%-3%;
    Ethylhexyl Glycerin 1%-3%;
    Potassium Sorbate 1%-3%;
    *Hamamelis Virginiana* Extract 0.1%-0.3%;
    Aloe Barbadensis Leaf Juice 0.1%-0.3%;
    Tocopheryl Acetate 0.1%-0.3%;
    Sodium Benzoate 0.1%-0.3%;
    Phenoxyethanol 0.1%-0.3%; and
    Citric Acid 0.1%-0.3%.

2. The method according to claim 1, wherein a plurality of toilet tissue squares are acquired and arranged in a stacked configuration.

3. The method according to claim 1, wherein in said orienting step the angle of orientation of the orifice is within the range of 30 degrees to 60 degrees.

4. The method according to claim 1, wherein in said orienting step the orifice is angled at 45 degrees with respect to the plane of the at least one toilet tissue square.

5. The method according to claim 1, wherein in said depressing the finger pump step, said finger pump is depressed three times to accumulate three spray mists on the at least one toilet tissue square.

6. The method according to claim 1, wherein in said depressing the finger pump step, said finger pump is depressed at least once to moisten a center section of the at least one toilet tissue square while leaving an outer outline portion dry.

7. The method according to claim 1, wherein said cleansing liquid additionally includes:
    Fragrance 0.1%-0.3%.

8. The method according to claim 1, wherein the cleansing liquid further includes fragrance, and wherein dispensing the cone of mist of the cleansing liquid toward the at least one toilet tissue square also disperses some of the fragrance into the air.

* * * * *